United States Patent
Jin et al.

(10) Patent No.: US 9,727,937 B2
(45) Date of Patent: *Aug. 8, 2017

(54) SECURE AND USABLE AUTHENTICATION FOR HEALTH CARE INFORMATION ACCESS

(75) Inventors: Hongxia Jin, San Jose, CA (US); Qihua Wang, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 545 days.

This patent is subject to a terminal disclaimer.

(21) Appl. No.: 13/593,251

(22) Filed: Aug. 23, 2012

(65) Prior Publication Data

US 2012/0323607 A1    Dec. 20, 2012

Related U.S. Application Data

(63) Continuation of application No. 12/855,855, filed on Aug. 13, 2010, now Pat. No. 8,533,800.

(51) Int. Cl.
| | |
|---|---|
| *G06Q 50/22* | (2012.01) |
| *G06F 19/00* | (2011.01) |
| *G06F 21/35* | (2013.01) |
| *G06F 21/31* | (2013.01) |
| *G06Q 50/24* | (2012.01) |
| *G06F 21/62* | (2013.01) |
| *H04L 9/32* | (2006.01) |

(52) U.S. Cl.
CPC .......... *G06Q 50/22* (2013.01); *G06F 19/322* (2013.01); *G06F 19/327* (2013.01); *G06F 21/31* (2013.01); *G06F 21/35* (2013.01); *G06F 21/6245* (2013.01); *G06Q 50/24* (2013.01); *G06F 2221/2111* (2013.01); *G06F 2221/2137* (2013.01); *H04L 9/3228* (2013.01); *H04L 9/3234* (2013.01); *H04L 2209/88* (2013.01)

(58) Field of Classification Search
CPC ...... G06Q 50/22; G06Q 50/24; G06F 19/322; G06F 19/327; G06F 21/31; G06F 21/6245

See application file for complete search history.

(56) References Cited

U.S. PATENT DOCUMENTS

| | | | | |
|---|---|---|---|---|
| H2120 | H * | 7/2005 | Cudlitz | 235/382 |
| 6,988,075 | B1 * | 1/2006 | Hacker | 705/3 |
| 7,676,380 | B2 * | 3/2010 | Graves et al. | 705/2 |
| 8,126,733 | B2 * | 2/2012 | Dicks et al. | 705/2 |
| 2002/0120472 | A1 * | 8/2002 | Dvorak et al. | 705/3 |
| 2003/0023461 | A1 * | 1/2003 | Quintanilla et al. | 705/3 |
| 2005/0240613 | A1 * | 10/2005 | Logan, Jr. | 707/102 |
| 2005/0268113 | A1 * | 12/2005 | Mahone et al. | 713/189 |

(Continued)

*Primary Examiner* — Minnah Seoh
*Assistant Examiner* — Jonathan Durant
(74) *Attorney, Agent, or Firm* — Shimokaji IP

(57) ABSTRACT

Embodiments of the invention relate to providing a health care provider access to an electronic record of a patient may be provided. A determination is made as to whether the health care provider is logged onto a computer system in a physical area assigned to the patient. Whether the health care provider is logged onto the computer system during working hours of the provider is also ascertained. The health care provider is provided with access to the electronic record of the patient via the computer system if the determining resolves to true and the ascertaining resolves to true.

8 Claims, 6 Drawing Sheets

(56) References Cited

U.S. PATENT DOCUMENTS

| | | | |
|---|---|---|---|
| 2006/0026035 A1* | 2/2006 | Younkes et al. | 705/2 |
| 2006/0143041 A1* | 6/2006 | Tipirneni | G06F 19/322 705/2 |
| 2006/0219776 A1* | 10/2006 | Finn | B60R 25/25 235/380 |
| 2006/0236373 A1* | 10/2006 | Graves et al. | 726/3 |
| 2007/0061169 A1* | 3/2007 | Lorsch | 705/3 |
| 2007/0067853 A1* | 3/2007 | Ramsey | 726/28 |
| 2007/0078677 A1* | 4/2007 | Hofstetter | 705/2 |
| 2007/0083445 A1* | 4/2007 | Garcia et al. | 705/32 |
| 2007/0106892 A1* | 5/2007 | Engberg | G06Q 20/02 713/168 |
| 2007/0136096 A1* | 6/2007 | Okalebo et al. | 705/2 |
| 2007/0186106 A1* | 8/2007 | Ting et al. | 713/168 |
| 2007/0204033 A1* | 8/2007 | Bookbinder et al. | 709/224 |
| 2008/0001752 A1* | 1/2008 | Bruns | G06Q 10/08 340/572.1 |
| 2008/0109895 A1* | 5/2008 | Janevski | G06F 21/35 726/19 |
| 2008/0159318 A1* | 7/2008 | Pierlot et al. | 370/412 |
| 2009/0112627 A1* | 4/2009 | Berkman et al. | 705/3 |

\* cited by examiner

SECURE AND USABLE AUTHENTICATION FOR HEALTH CARE INFORMATION ACCESS

RELATED APPLICATIONS

The present continuation application claims benefit of U.S. application Ser. No. 12/855,855, filed Aug. 13, 2010, which application is incorporated herein by reference in its entirety.

BACKGROUND

The present invention generally relates to securing sensitive information and more specifically relates to secure and usable authentication for health care information access.

In the course of providing health care to patients, health care providers such as hospitals, medical offices, doctors, and nurses will document relevant patient information such as a patient's medical history and the patient's course of care for each patient in a patient's medical records. The purpose of keeping a medical record for a patient includes allowing subsequent health care providers who are treating the patient to provide continuity of care to that patient.

Because a patient's medical record is highly sensitive, great care must be taken to ensure that a patient's medical record is available to an authorized doctor or nurse only when the doctor or nurse needs it in order to treat the patient. However, the layers of security implemented to protect the patient's medical record may often make it cumbersome for the doctor or nurse to quickly and easily access the patient's medical record, thus causing the doctor or nurse to unnecessarily waste time and possibly inconveniencing the patient in order to gain access to the patient's medical records.

BRIEF SUMMARY

In one aspect of the present invention, a method comprises determining if a health care provider is logged onto a computer system in a physical area assigned to a first patient, ascertaining if the health care provider is logged onto the computer system during working hours of the health care provider, and if the determining resolves to true and the ascertaining resolves to true, providing the health care provider with access to an electronic record of the first patient using the computer system.

In another aspect of the present invention, a system comprises a device authentication module that authenticates a portable wireless device associated with a health care provider and a record access module that determines if the health care provider is logged onto a computer system in a physical area assigned to a first patient. If the device authentication module successfully authenticates the portable wireless device and if the record access module successfully determines that the health care provider is logged onto the computer system in the physical area assigned to the first patient, the health care provider is granted access to the electronic record of the first patient using the computer system In another aspect of the present invention, a computer program product comprises a computer readable storage medium having computer readable program code embodied therewith. The computer readable program code comprises computer readable program code configured to determine if a health care provider is logged onto a computer system in a physical area assigned to a first patient, computer readable program code configured to ascertain if the health care provider is logged onto the computer system during working hours of the health care provider, and, if the determining resolves to true and the ascertaining resolves to true, computer readable program code configured to provide to the health care provider access to the electronic record of the first patient via the computer system.

These and other features, aspects and advantages of the present invention will become better understood with reference to the following drawings, description and claims.

DETAILED DESCRIPTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

Broadly, embodiments of the present invention generally provide a secure and usable authentication mechanism for health care environments by combining time and location-based access control with the use of hands-free portable wireless devices to ensure that patient medical records may be better protected from unauthorized access while at the same time making it easier for authorized health care providers to access the patient medical records.

Increasingly, health care systems, such as hospitals, are storing patient information, such as a patient's medical records, electronically onto a computer system or server. The electronic medical records stored on the computer system may be secured so that only certain authorized users are able to access and view the stored medical records. One common method for securing electronic information, such as the electronically stored medical records, may be to require a user trying to access the system to log into the system by inputting a password. Once the user has logged into the system by inputting his password, the system may determine the medical records that the user is allowed to access and any medical records that the user is not allowed to access based on the privileges granted to the user in the system.

Figure 1:
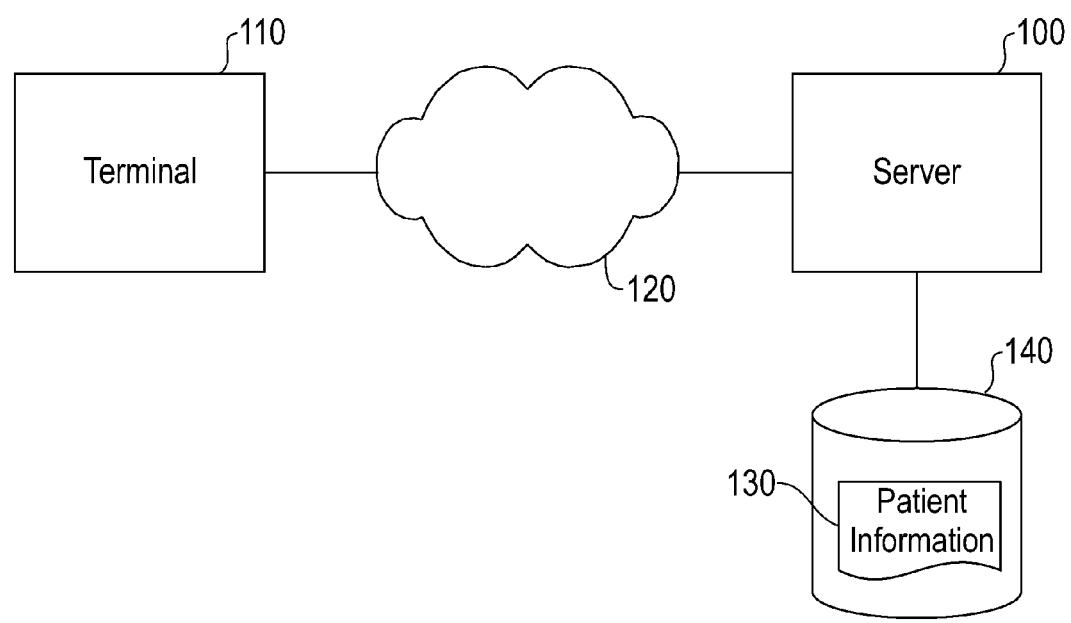
FIG. 1 shows a schematic view of a patient information security system in accordance with an embodiment of the present invention.

With reference to FIG. 1, a terminal 110, such as a desktop computer, laptop computer, tablet, smart phone, or any other hardware and/or software or firmware device, may be able to communicate with a server 100 over a network 120, such as the Internet or other wired or wireless network, in order to access patient information 130 stored in a patient information database 140 on a computer readable storage medium. A user may log into the server 100 by inputting a password into the terminal 110 and sending the password from the terminal 110 to the server 100. The server 100 may authenticate the user based on the inputted password and may determine whether the user has permission to access the patient information 130. If the server 100 determines that the user has permission to access the patient information 130, the server 100 may send the patient information 130 through the network 120 to the terminal 100 for display to the user. In a hospital environment, terminals 110 may be placed through out the hospital, and a user may use any terminal 110 in the hospital to access the patient information 130 by entering his password into the terminal 110.

While the above-described username and password security approach is a tried-and-true strong authentication approach, there may also be drawbacks to the above-described security approach when such an approach is used in a hospital. For example, users may sometimes forget to log out of the server 100 after viewing the patient information 130. The problem of users forgetting to log out of the server 100 may be even more prevalent in a hospital setting, as doctors are often very busy and may have to rush from one room to another. If a doctor rushes away from the terminal 110 before he has logged out, then an unauthorized user may be able to use the unattended terminal 110 to view the patient information 130.

One remedy to the problem of doctors or other authorized healthcare providers forgetting to log out may be to set an inactivity timeout so that after a period of inactivity the system may automatically log the user out of the system. However, it may be difficult to find an ideal timeout period in the context of a healthcare system. For example, if the timeout period is too short, then a user may have to re-log on several times during a single session. Conversely, if the timeout period is too long, then the session may not time out until well after the user has left the terminal 110, thus leaving unresolved the problem of the unattended terminal 110.

In addition, it may not be very user friendly in a hospital environment to require a user to type their username and password using a computer keyboard in order to input that information to the terminal 110. For example, doctors may often wear gloves that may make typing more cumbersome if not impossible. Further, having to manually log into the terminal 110 may also be very time consuming.

To address some of the drawbacks of the username and password security approach, a badge-based security approach may be implemented in hospitals in order to provide a more user-friendly way to authenticate users so that authorized users may be able to log into a system in order to view patient information without having to type in a username and password.

Currently, doctors and nurses, as well as many other professionals in other fields, may routinely carry badges while at their workplace to identify themselves. Some of these badges may be used by the badge holder to gain access to certain secured areas, or may be used to track the location of the badge holder via a portable wireless device, such as a radio-frequency identification (RFID) tag or a proximity card, embedded in the badge. In addition, people generally keep the badges with them at all times at the workplace, thus allowing their movements to be tracked based on the location of their badge. Thus, a security approach incorporating badges may allow a doctor to authenticate himself via a badge. In a badge-based security approach, the terminal 110 may include a sensor or badge reader that may detect that a badge is in close proximity to the terminal 110, and log the owner of the badge directly into the system without the need to type in a password, thus allowing a doctor to log into a terminal 110 in a hands-free fashion.

Figure 2:
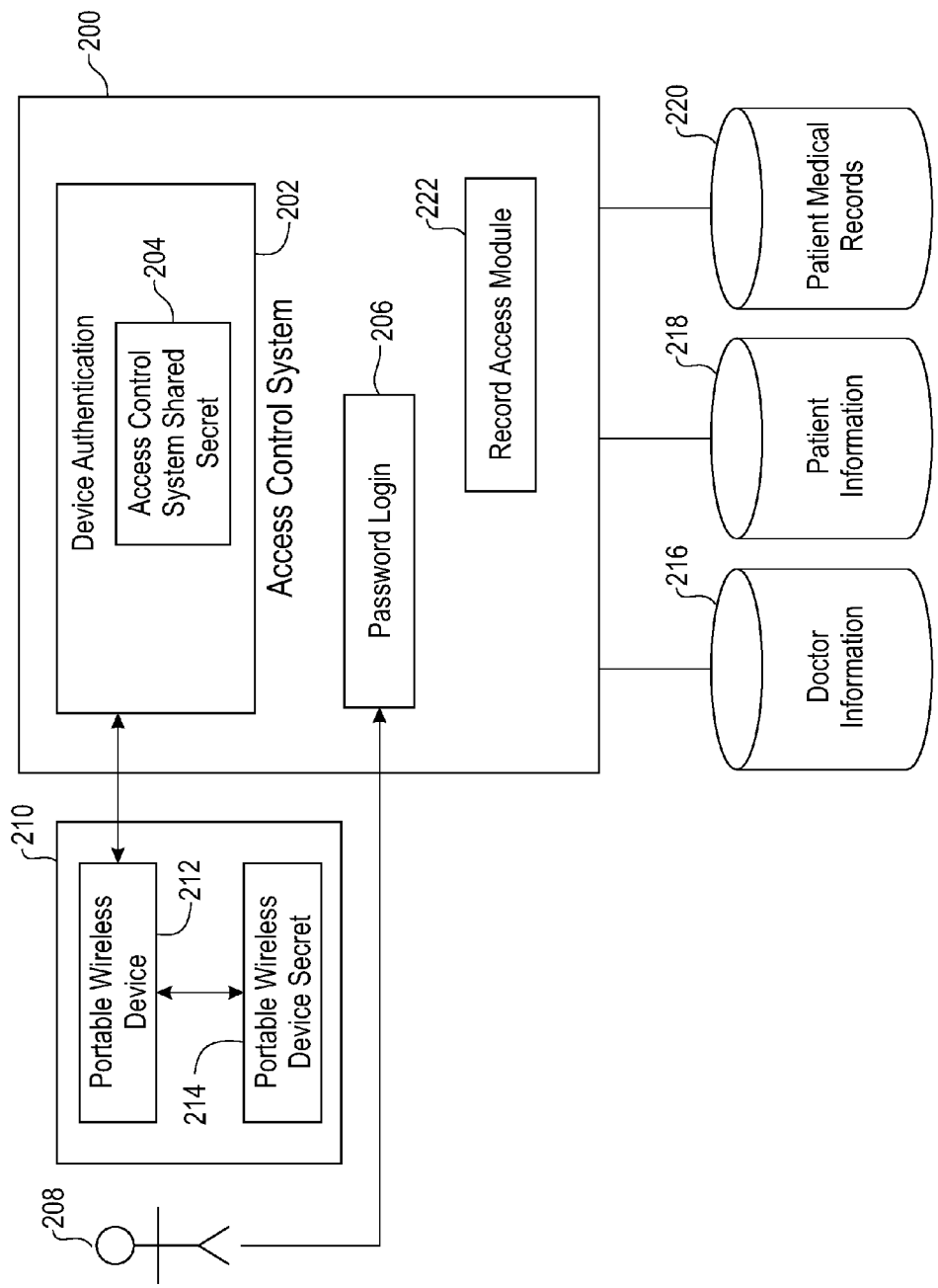
FIG. 2 shows a schematic view of an access control system in accordance with an embodiment of the present invention.

With reference to FIG. 2, a badge-based authentication approach may be used along with a password-based authentication approach to access patient medical records 220 protected by an access control system 200. A user 208 may enter a password that may be authenticated by the password login module 206 within the access control system 200. If the password login module 206 determines that the entered password is correct, the access control system 200 may grant the user 208 access to patient medical records 220.

Alternatively, the user 208 may use a badge 210 to automatically authenticate with the access control system 200 in order to gain access to patient medical records 220. The badge 210 may include a portable wireless device 212, such as an RFID tag, that may either directly or indirectly, such as through an intermediary terminal with an RFID reader, communicate with the device authentication module 202 within the access control system 200. The device authentication module 202 may use a shared secret scheme to compare the access control system shared secret 204 in the device authentication module 202 with the portable wireless device secret 214 in the badge 210 in order to verity the badge 210. If the badge 210 is successfully verified, such as by the device authentication module 202 determining that the portable wireless device secret 214 is the same as the access control system shared secret 204, the records access module 222 in the access control system 200 may determine one or more patient medical records 202 that the user 208 is entitled to view, based upon doctor information 216, such as the working hours and the current location of the user 208 and the patient information 218, such as a patient's current location.

Because badges may make it easier for doctors to access patient information by automating the process of authenticating doctors with the access control system that secures patient medical records, doctors' badges may become enticing targets for malicious entities wishing to steal patient information because it may be easier for malicious entities to steal badges than to steal a doctor's password. A solution to this problem may be based on the observation that health care facilities, such as hospitals, may often provide a special working environment for doctors. During the course of a working day, a doctor working at a hospital may often access different patient information at different places and different times. For example, a doctor may go from one hospital room to another to treat or examine patients checked into the hospital rooms. However, a doctor at a hospital may rarely access multiple patients' information at the same time because a doctor may usually only treat or examine one patient at a time. Further, a doctor at a hospital may also rarely access patient records outside of his working day. Based on these observations, a time- and/or location-based access control mechanism may be used to minimize the damage caused by a lost or stolen badge.

A time-based access control mechanism may limit the time when a doctor may use his badge to authenticate himself. For example, the doctor may be limited to using his badge to access patient information only during his work hours. Thus, for example, if a doctor is scheduled to work from 9 a.m. to 5 p.m., the access control mechanism may ascertain whether the doctor is trying to access patient information during his working hours of 9 a.m. to 5 p.m. and may, for example, disallow that doctor's badge for authentication purposes before 9 a.m. and after 5 p.m. The time-based access control mechanism may also be flexible in order to accommodate doctors that might not finish up with their work until after their scheduled work hours. For example, if a doctor scheduled to work until 5 p.m. is still accessing patient records at 4:40 p.m., 4:50 p.m., and 5 p.m., and then requests access to patient records at 5:10 p.m., the system may grant the doctor's request for access even though 5:10 p.m. is past the doctor's working hours. The system may grant this after-hours access because the doctor has been continuously accessing patient records shortly before the request for access at 5:10 p.m., and thus the system may automatically extend the doctor's access. Conversely, if the same doctor requests access to patient records at 6 p.m. when he had last accessed patient records at 4:50 p.m., the doctor may be required to log in using his password because 6 p.m. is past his working hours and he has not been accessing patient records in the past hour.

The time-based access control mechanism may help to protect against lost, stolen, or ghosted and leeched badges because a malicious entity that wants to use a stolen badge to access and steal patient medical records may have to know the badge owner's work schedule and perform an attack using the stolen badge within the work schedule, as the badge may not be successfully authenticated outside of the badge owner's work hours.

Figure 3:
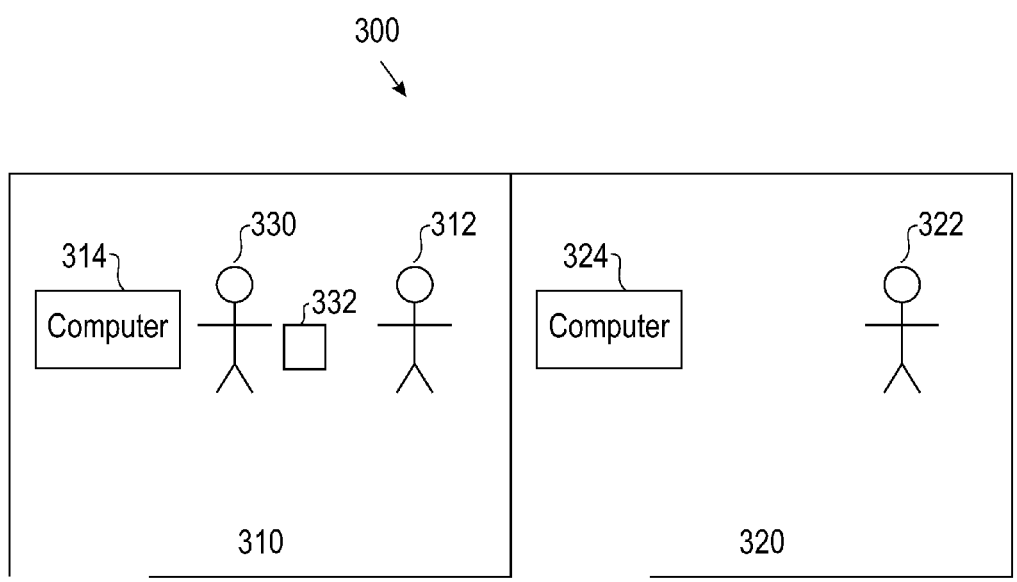
FIG. 3 shows two rooms of a health care facility in which an embodiment of the present invention may be used.

A location-based access control mechanism may limit the doctor's ability to access patient medical records based on the location of the doctor. FIG. 3 shows two rooms of a health care facility 300 in accordance with an embodiment of the present invention. A first patient 312 may reside in a first room 310 of the facility 300 while a second patient 322 may reside in a second room 320 of the facility 300. The first room 310 of the facility 300 may also have a first computer 314 usable to look up patient medical records while the second room 320 of the facility 300 may also have a second computer 324 also usable to look up patient medical records. A health care provider, such as a doctor 330, may be assigned to treat and examine the patients 312 and 322 by visiting the patients 312 and 322 in their rooms 310 and 320. In order for the doctor 330 to access medical records for a patient, it may be required for the doctor 330 to log onto the computers 314 and 324.

The location-based access control mechanism may impose a limitation that allows the doctor 330 to access a patient's medical records only from a computer located in the room where that patient is residing. When the doctor 330 wearing a badge 332 enters the first room 310 to treat or examine the first patient 312, the badge 332 worn by the doctor 330 may be detected by the first computer 314 as being in the first room 310, and may therefore cause automatic login of the doctor 330 into a patient records system via the first computer 314. The doctor 330 may use the first computer 314 to make a request for access for patient medical records regarding the first patient 312. When the patient records system receives the request, the system may determine that the first patient 312 is residing in the first room 310, and may make a determination as to whether the doctor 330 is using a computer in the first room 310 to access medical records regarding the first patient 312. Because the first computer 314 resides within the first room 310, the system may allow the doctor 330 to access the first patient's medical records.

However, if the doctor 330 uses the first computer 314 in the first room 310 to make a request for access to medical records of any other patient besides the first patient 312, such as the second patient 322 residing in the second room 320, the system may deny the doctor 330 access to the second patient's medical records because the first computer 314 used by the doctor 330 to access the second patient's medical records is not in the second room 320 that the second patient 322 is residing in.

Once the doctor 330 has finished treating or examining the first patient 312, the doctor 330 may leave the first room 310. Once the doctor 330 leaves the first room 310, the badge 332 worn by the doctor 330 may be detected as being outside of the first room 310, and may thereby cause the doctor 330 to be automatically logged off of the first computer 214.

The location-based access control mechanism may also allow a doctor whose badge is detected as being in his own secure office to be able to access the medical records of any of his patients, because it may be assumed that the doctor's office is secure and may be kept locked when not used by the doctor, and thus may be considered a more secure location than a patient's room or other public areas of a hospital.

The time-and-location-based access control mechanisms may also be implemented in outpatient situations where patients that go to a hospital or other health care facility to visit a doctor for treatment and/or examination leave after their doctor's visit. If a doctor in an outpatient situation works in one examination room or switches between multiple rooms during the day, the doctor may be limited to accessing patient medical records only while in those rooms. Furthermore, the doctor may also be limited to only accessing the medical records of patients scheduled to visit the doctor that day, and the doctor may be denied access to a scheduled patient's medical records until that patient arrives at the hospital. For example, a nurse working with the doctor may enable access to a patient's medical records after the nurse sees that the patient has checked into the hospital, and the nurse may set an end time for access to the patient's medical records based on the nurse's estimate of how long the patient's appointment might take. Further, if the doctor switches from accessing a first patient's medical records to accessing a second patient's medical records, the access control system may disallow the doctor's access to the first patient's medical records, so that the doctor may be allowed to access only one or a pre-specified very limited number of patients' medical records at any given time.

The restrictions imposed by the time-and-location-based access control mechanisms may be limited to situations when the doctor is authenticated via his badge. If the doctor authenticates himself by using a password, this may bypass the time-and-location-based access control mechanisms to allow the doctor to access a patient's medical records regardless of the doctor's work hours or location. Thus, flexibility may be provided to the doctor in exceptional situations, such as during the course of an emergency in order to look up patient records outside of the patient's room or in cases where the doctor may need to access patient information at an unusual time or an unusual way not allowed by the badge's time-and-location-based access control mechanisms.

The location-based access control mechanism may help to protect against lost, stolen, or ghosted and leeched badges by making it more cumbersome and time consuming for a malicious entity to access large numbers of patient medical records using a stolen badge. Instead of being able to access medical records of multiple patients at a single computer, the malicious entity with a stolen badge may have to physically move from room to room to access each patient's medical records. Furthermore, if it is determined that a badge has been used in too many different rooms to access more than a particular number of patient medical records in less than a particular time period, the abnormal access pattern of the badge may be detected by an intrusion detection system and the badge may be remotely deactivated.

The particular time period and the threshold number of patient medical records accessed used by the intrusion detection system may be customized according to a particular situation. For example, a hospital might determine that a doctor at that hospital is estimated to spend at least fifteen minutes with each patient. Therefore, if it is detected that a doctor's badge has been used to access more than two patient medical records within a fifteen minute period, then the intrusion detection system may remotely deactivate that doctor's badge unless it is determined that the doctor is accessing those records in his office.

Figure 4:
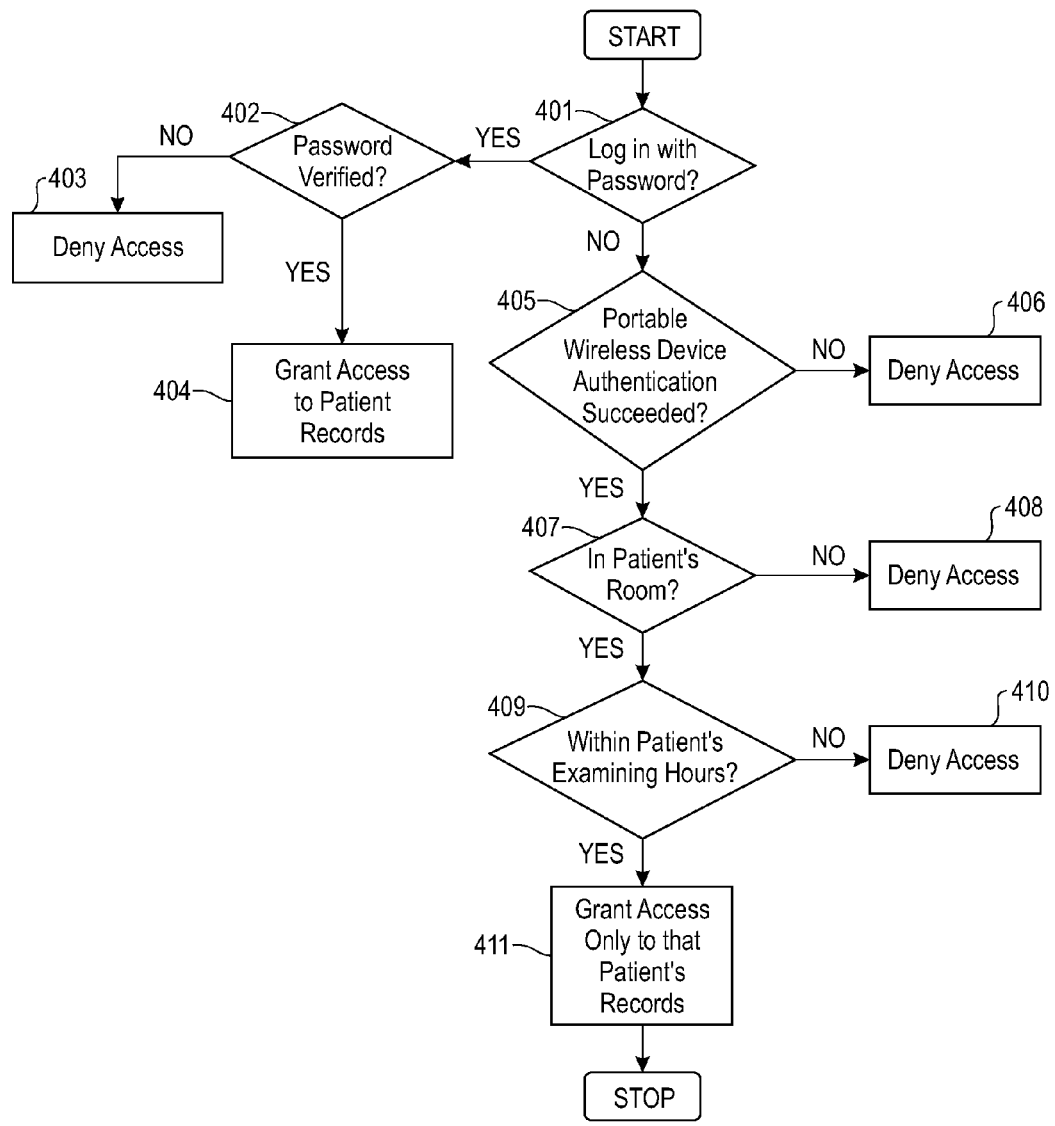
FIG. 4 shows a flowchart of an access control process in accordance with an embodiment of the present invention.

FIG. 4 shows a flowchart of an access control process in accordance with an embodiment of the present invention. At 401, a determination may be made about whether a doctor has chosen to log into the access control system with a password. If the determination at 401 is true, at 402 the password may be verified, such as by comparing the entered password with a copy of that doctor's password stored in the access control system. If the password is verified, at 404 the doctor may be granted access to patient medical records. If, on the other hand, the password is incorrect, at 403 the doctor may be denied access to any patient medical records.

If the determination at 401 is false, at 405 a determination may be made about whether a portable wireless device, such as an RFID tag on the doctor badge, has successfully authenticated with the access control system. If the portable wireless device authentication was not successful, at 406 the doctor using the portable wireless device may be denied access.

On the other hand, if the portable wireless device has successfully authenticated with the access control system, at 407 it may be determined whether the doctor is in a specific patient's room. Such a determination may be made by seeing if a doctor is logged onto a computer located in the specific patient's room. If the doctor is not in that specific patient's room, at 408 the doctor may be denied access to that patient's medical records. If the doctor has been determined as being in that specific patient's room, at 409 a determination may be made about whether the doctor is trying to access patient medical records within the examining hours of the patient in the same room as the doctor. If it is not within that patient's examining hours, at 410 the doctor may be denied access to that patient's medical records. If it is determined that it is within that patient's examining hours, at 411 the doctor may be granted access only to the medical records of the patient that is in the same room as the doctor.

Figure 5:
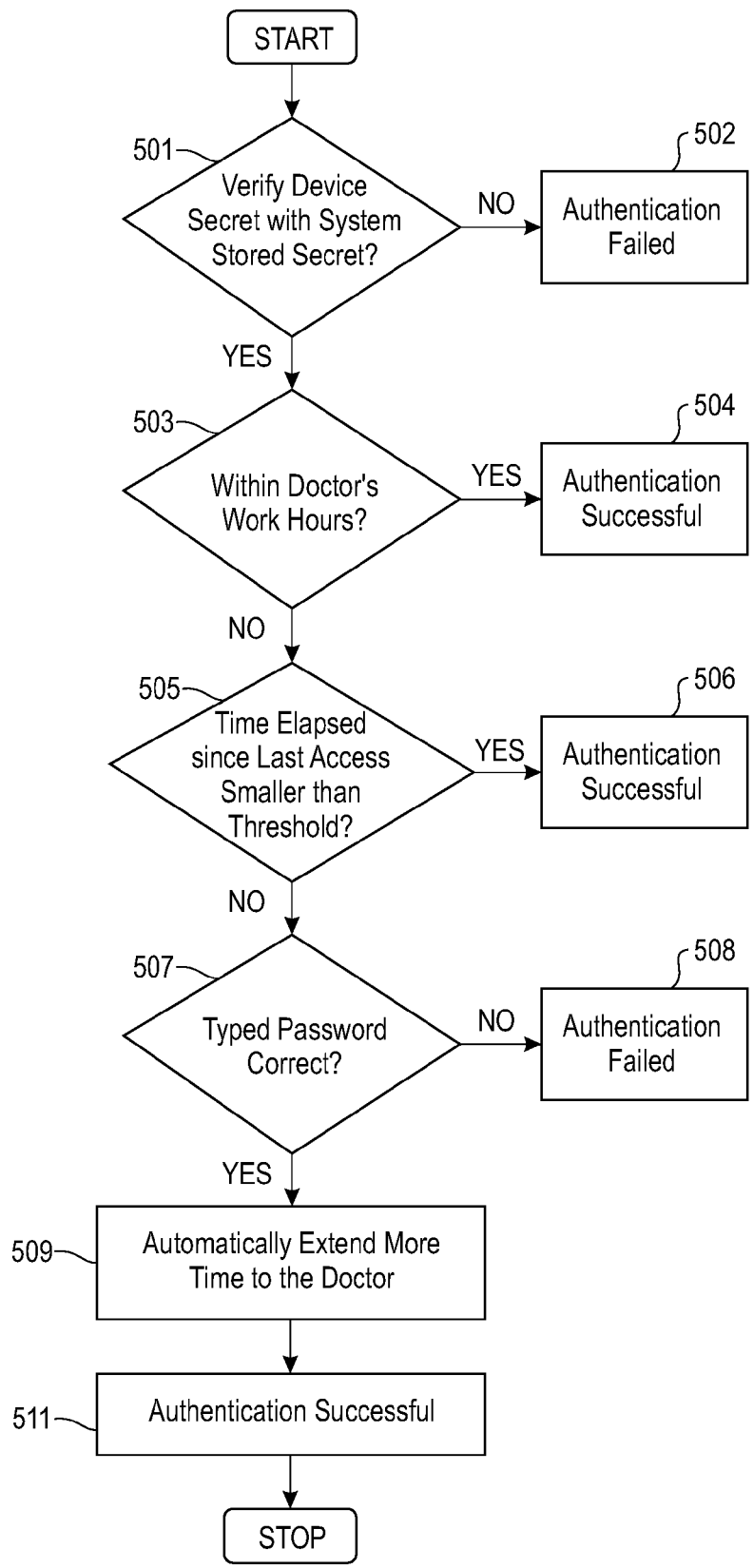
FIG. 5 shows a flowchart of the process of authenticating the portable wireless device in accordance with an embodiment of the present invention.

FIG. 5 shows a flowchart of the process of authenticating a portable wireless device, such as a RFID tag on a doctor's badge, in accordance with an embodiment of the present invention. A doctor's badge may be read by a tag reader on a computer system that the doctor is using, and data from that badge may be sent from the computer system to a server for authentication. To secure a portable wireless device, a piece of data called a shared secret may be stored on the portable wireless device. At 501, the shared secret on the portable wireless device may be verified to determine if it is the same as the shared secret stored on the access control system. If the shared secret is not the same, at 502 the authentication process may fail.

If it is determined that the shared secret is the same, at 503 a determination may be made whether a request for access is being made within the working hours of the doctor whose badge's portable wireless device is being authenticated. If the determination at 503 resolves to true, at 504 the authentication process may succeed.

If it is determined that the request for access is being made outside of the doctor's working hours, at 505 a determination may be made about whether the time that has elapsed since the doctor last accessed a patient's medical records is smaller than a certain threshold, such as an hour since last access. If the determining at 505 resolves to true, it may mean that the doctor is simply continuing to work past the end of the working day, and that for the doctor's convenience his working hours should be automatically extended. Thus, at 506, the portable wireless device within the doctor's badge may be successfully authenticated.

If, on the other hand, it is determined at 505 that the time elapsed since when the doctor last accessed a patient's medical records is larger than the certain threshold, at 507 the doctor may be required to type in his password and a determination may be made about whether the password is correct. If the password is incorrect, at 508 the authentication may fail. If at 507 it is determined that the password is correct, at 509 the doctor's working day may be automatically extended for a particular amount of time, such as one more hour, and the doctor's records may be updated in the access control system may be updated to reflect the extended working day. At 511, the authentication may be deemed successful because the entered password was correct.

Figure 6:
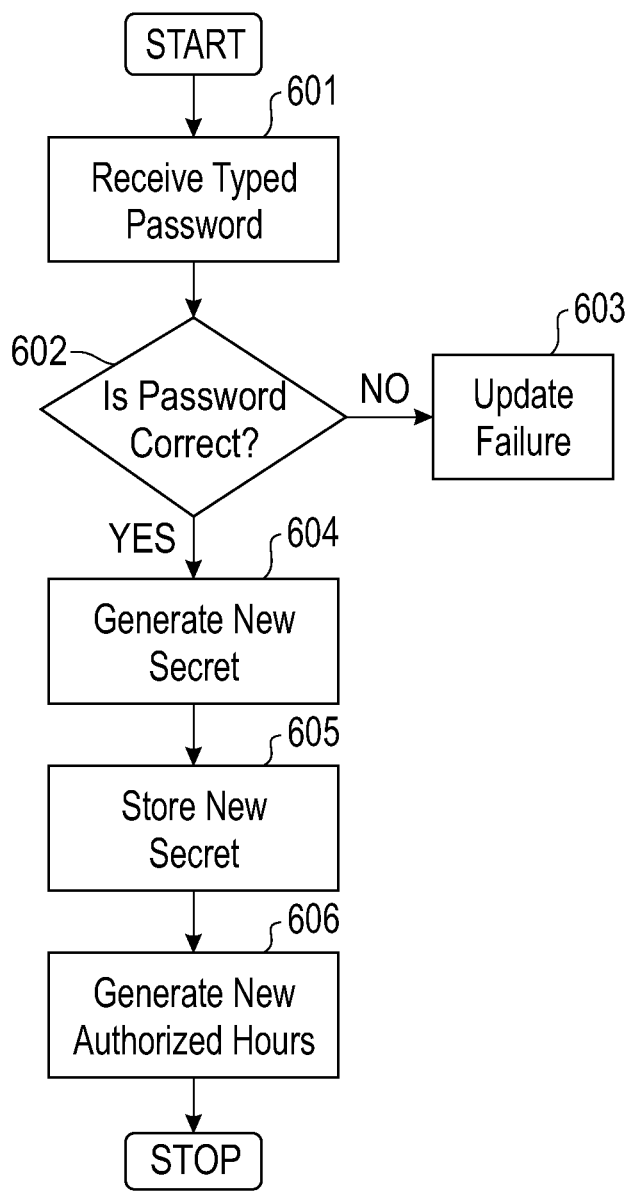
FIG. 6 shows a flowchart of the process of updating the portable wireless device's secret in accordance with an embodiment of the present invention.

FIG. 6 shows a flowchart of the process of updating the portable wireless device's secret data in accordance with an embodiment of the present invention. As mentioned above in describing FIG. 5, a shared secret key approach may be used to authenticate the portable wireless device by storing a secret data within the portable wireless device. To increase security, the secret data may be changed regularly, such as being changed daily, so that a portable wireless device with an out-of-date secret data may not be usable to access patient medical records.

At 601, a doctor updating his portable wireless device's secret key may be prompted to type in his password at a computer connected to the access control system, and the access control system may receive the typed password from the computer. At 602, a determination may be made as to whether the typed in password is correct. If the password is not correct, at 603 the portable wireless device may fail to update its secret data. If the password is correct, at 604 a new secret data may be generated and at 605 the new secret data may be stored on the portable wireless device as well as the access control system. At 606, the new authorized hours of the new secret data may be generated, after which another new secret data may need to be generated.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction processing system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction processing system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may run entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which runs via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which run on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more runnable instructions for implementing the specified logical function(s). It should also be noted that, in some alternative implementations, the functions noted in the block may occur out of the order noted in the figures. For example, two blocks shown in succession may, in fact, be run or processed substantially concurrently, or the blocks may sometimes be run or processed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be understood, of course, that the foregoing relates to exemplary embodiments of the invention and that modifications may be made without departing from the spirit and scope of the invention as set forth in the following claims.

What is claimed is:

1. A method, comprising:
using a radio frequency tag secured to a badge, wherein the badge is configured to:
utilize a card authentication protocol to authenticate the radio frequency tag, wherein the card authentication protocol comprises a time-based shared secret stored in the radio frequency tag that is changed on a regular basis, and the radio frequency tag is authenticated by the radio frequency tag communicating with an authentication module on a computer system;
sense a proximity of the badge to the computer system by utilizing a proximity sensor attached to the computer system, wherein the proximity sensor is configured to sense proximity of the badge to the computer system;
verify that the shared secret stored on the radio frequency tag is the same as a system secret stored on the computer system;
in response to the shared secret being the same as the system secret:

determine whether the health care provider is in a physical area assigned to a first patient by:
sending a radio frequency signal identification information of the health care provider from the radio frequency tag to the authentication module with a tag reader on the computer system, wherein the radio frequency tag determines the position information of the health care provider based on proximity to a terminal of the computer system,
comparing the position of the terminal of the computer system with position information of the physical area assigned to the first patient; and
comparing position information of the health care provider with position information derived from the computer system of the physical area assigned to the first patient stored on the computer system;
periodically estimating an appointment time period for the health care provider with the one of the plurality of patients;
denying the health care provider access to an electronic record of the first patient if the health care provider is logged onto the computer system in a physical area assigned to the first patient outside the periodically estimated appointment time period for the first patient;
wherein the radio frequency tag is configured to automatically log in the health care provider to the computer system in response to the health care provider being in the physical area assigned to the first patient;
wherein the computer system is configured to determine whether the health care provider is logged onto the computer system at a time the health care provider is in the physical area assigned to the first patient;
wherein the computer system is configured to ascertain whether the health care provider is logged onto the computer system during authorized hours of the health care provider;
wherein the computer system is configured to, in response to the health care provider being logged onto the computer system at the time the health care provider is in the physical area assigned to the first patient, and in response to the health care provider being logged onto the computer system during the authorized hours of the health care provider, provide the health care provider with access to the electronic record of the first patient using the computer system by transmitting authorization for the health care provider to the computer system, thereby providing visual access to the electronic record of the first patient on a computer display of the computer system;
the computer system is configured to automatically generate a new shared secret, a new system secret, and new authorized hours for the health care provider in response to the health care provider accessing a system to update the shared secret;
whereby the electronic record of the first patient is available to the health care provider only when the health care provider needs it in order to treat the first patient;
whereby the health care provider is directly logged into the computer system without the need to type in a password, thus allowing the health care provider to log into the terminal of the computer system in a hands-free fashion; and
wherein the computer system is configured to log the health care provider out of the computer system after a predetermined time period of inactivity by the health care provider on the computer system.

2. The method of claim 1, further comprising:
the computer system being further configured to:
detect the health care provider in the physical area assigned to the first patient;
log the detected health care provider onto the computer system in the physical area assigned to the first patient; and
log the health care provider off of the computer system in the physical area assigned to the first patient in response to the health care provider being no longer detected in the physical area assigned to the first patient.

3. The method of claim 2, wherein the computer system is configured to detect that a portable wireless device assigned to the health care provider is near the computer system.

4. The method of claim 1, further comprising:
the computer system is further configured to, in response to the health care provider previously being logged onto the computer system, determine an elapsed time to when the health care provider last accessed the electronic records of the first patient; and
extend the new authorized hours by a particular amount of time in response to the elapsed time being less than a maximum time period.

5. The method of claim 1, further comprising:
the computer system being further configured to, in response to the health care provider having had access to more than a particular number of electronic records of patients in less than a particular amount of time, deny the health care provider access to the electronic record of the first patient.

6. The method of claim 1, further comprising:
the computer system being further configured to, in response to a second patient not being assigned to the area assigned to the first patient, deny the health care provider access to a second electronic record of the second patient via the computer system.

7. The method of claim 1 further comprising:
the computer system being further configured to, in response to the health care provider using a computer system assigned to the health care provider and the health care provider being in an office assigned to the health care provider, provide to the health care provider access to the electronic record from the assigned computer system.

8. The method of claim 1, further comprising:
the computer system being further configured to, in response to the health care provider inputting the password that allows the health care provider to log onto the computer system of the health care organization of which the health care provider is a member, allow the health care provider to access the electronic record of the first patient via the computer system of the health care organization.

* * * * *